United States Patent
Jaffe (10) Patent No.: US 6,821,748 B1
(45) Date of Patent: Nov. 23, 2004

(54) DETERMINATION OF CYTOTOXIC SUBSTANCES IN WHOLE EFFLUENT SAMPLES

(76) Inventor: Robert L. Jaffe, 45-10 Court Sq., Long Island City, NY (US) 11101

( * ) Notice: Subject to any disclaimer, the term of this patent is extended or adjusted under 35 U.S.C. 154(b) by 520 days.

(21) Appl. No.: 09/086,138

(22) Filed: May 28, 1998

(51) Int. Cl.$^7$ ................................................. C12Q 1/18
(52) U.S. Cl. .......................................... 435/32; 435/29
(58) Field of Search ............................. 435/32, 29, 30, 435/258.1, 262, 947, 202

(56) References Cited

U.S. PATENT DOCUMENTS 5,387,508 A * 2/1995 Jaffe ............................ 435/32

OTHER PUBLICATIONS

Jaffe, R. Rapid Assay of Cyotoxicity Using Tetramitus Flagellates. Toxicology and Industrial Health 11(5)543–58, Sep. 95.*

Phillips, D.J.H., "The Use of Biological Indicator Organisms to Monitor Trace Metal Pollution in Marine and Estuarine Environments—A Review", Environ. Pollut. 13:281–317, 1977.

Duez, R., et al., "Use of an *Amoeba proteus* model for in vitro cytoxicity testing in phytochemical research. Application to *Euphorbia hirta* extracts", Journal of Ethonopharmacology, 34:235–246, 1991.

Whong, W-Z., et al., "Development of an in situ microbial mutagenicity test system for airborne workplace mutagens: laboratory evaluation", Mutation Research, 130:45–51, 1984.

Hillebrandt, S. and I. Muller, "Repair of damage cause by UV– and X–irradiation in the amoeboflagellate *Maegleria gruberi*", Radiat Environ Biophys, 30:123–130, 1991.

Fulton, C., "Transformation of Tetramitus Amebae into Flagellates", Science 167:1269–1270, 1970.

Fulton, C., "Amebo–flagellates as Research Partners: The Laboratory Biology of Naegleria and Tetramitus", in Methods in Cell Physiology, vol. IV, ed. D.M. Prescott, Academic Press, New York, pp. 341–476, 1970.

Ashby, J. and R.W. Tennant, "Chemical structure, Salmonella mutagenicity and extent of carcinogenicity as indicators of genotoxic carcinogenesis among 222 chemicals tested in rodents by the U.S. NCI/NTP", Mutation Research 204:17–115, 1988.

* cited by examiner

*Primary Examiner*—Ralph Gitomer
(74) *Attorney, Agent, or Firm*—Oppedahl & Larson LLP (57) ABSTRACT

Cytoxotixc agent, and particularly DNA-damaging agents, can be detected in a whole effluent water or liquid sample by a method called whole effluent toxicity. A living culture of a particle-feeding flagellate is added to a sample, a growth rate is determined for the flagellate, and the growth rate is compared within the sample and its standard growth rate. A decrease in growth rate is indicative of cytotoxic agents in the sample.

15 Claims, 7 Drawing Sheets

DETERMINATION OF CYTOTOXIC SUBSTANCES IN WHOLE EFFLUENT SAMPLES

This application relates to the detection of cytotoxic substances and DNA damaging agents in whole effluent samples.

Detection of cytotoxic or DNA damaging agents in environmental samples (i.e., air, water, sewage or commercial effluent, or biological samples and the like) is an important aspect of pollution monitoring and control. In addition, the testing of control samples created in the laboratory is useful to assess the importance of any given material as a pollutant to be regulated or as a potential cytotoxic agent for pharmacological applications.

For many years, environmental testing and government regulation in the United States has focused on monitoring for discharge of individual chemical species. Recently, however, the US Environmental Protection Agency has recognized that this form of testing may be insufficient in some instances, and has approved so-called "whole effluent toxicity" (WET) test procedures. Such tests are appropriate because effluent limitations on specific compounds do not necessarily provide adequate protection for aquatic life when the toxicity of effluent components is not known, effects of effluent components are additive, synergistic, or antagonistic, and/or when an effluent has not been chemically characterized.

The EPA manual (EPA/600/4-90/027F) describes tests for effluents and receiving waters, and includes guidelines for the following areas: Laboratory safety; quality assurance; facilities and equipment; effluent sampling and holding times; dilution water; test species selection, culturing, and handling; data collection, interpretation and utilization; report preparation; and dilutor and mobile toxicity test laboratory design. The acute toxicity tests in the manual generally involve exposure of any of 20 test organisms to each of five effluent concentrations and a control water. The test duration depends on the objectives of the test and the test species, and ranges from 24–96 hours. The manual includes a list of freshwater and marine test organisms, and specified test conditions for 10 commonly used freshwater and marine organisms—*Cerodaphnia dubia*, *Daphnia magna*, *Daphnia pulex*, fathead minnows (*Pimephales promelas*), rainbow trout (*Oncorhynchus mykiss*), brook trout (*Saivelinus fontinalis*), mysids (*Mysidopsis bahia* and *Holmesimysis costata*), Bannerfish shiners (*Notropis leedsi*), sheepshead minnows (*Cyprinodon variegatus*), and silversides (*Menida menidia, M. beryllina,* and *M. peninsulae*). The tests are used to determine the effluent concentration, expressed as a percent volume, that within the prescribed test period causes death in 50% the organisms (LC50), or whether survival in a given (single) concentration of effluent, or in receiving water, is significantly different than in controls. Where death is not easily detected, e.g., with some invertebrates like *Ceriodaphnia* and *Daphnia* (water fleas), immobilization is considered equivalent to death.

While the goal of evaluating whole effluent toxicity is a laudable one, the relatively advanced organisms used in the established testing procedures tend to make such procedures expensive to perform. Furthermore, because the testing is based upon a determination of the number of individuals that die, the statistics tend to be quantized (each organism is either dead or not dead) which means that very large numbers of organisms are required to get good statistical results. Furthermore, in the case of the simpler organisms, the methods require interpretation (is that *Daphnia* really not moving?) which may result in inconsistent results, and which requires a level of skill which increases the cost of implementing the test. Thus, it would be desirable to have a test methodology for whole effluent toxicity that makes use of an organism that is culturable, and that provides results which are unquantized, require less skill in interpretation and can be performed more frequently.

U.S. Pat. No. 5,387,508, which is incorporated herein by reference, describes a test for detection of cytotoxic substances in environmental samples using flagellate *Tetramitus rostratus*. These tests measure variations in cell division rate of the *T. rostratus* flagellates, as well as organism death and are applicable to solid, liquid or gaseous samples, including waste water samples. In each of the specific examples for analysis of a liquid sample (water or urine samples), the sample is first treated to concentrate organic compounds found in the sample by absorption on a resin, extraction and evaporation to dryness. Thus, there is no disclosure of a WET test in which all of the potentially toxic substances from the sample are evaluated in natural combination.

SUMMARY OF THE INVENTION

It has now been found that particle-feeding flagellate protozoa, including for example *T. rostratus* in the flagellate form, can in fact be used to determine whole effluent toxicity in liquid effluent samples, including water and sewage samples, without any requirement for concentration of the sample. Thus, in accordance with the present invention, there is provided a method for evaluating a sample for the presence of cytotoxic substances comprising the steps of:

(a) obtaining a sample for testing containing a plurality of potentially cytotoxic substances;

(b) combining the sample, either directly or after an optional filtration step, with a culture of particle-feeding flagellate; and (c) monitoring the growth of the particle-feeding flagellate culture in the presence of the sample, wherein a decrease in growth of the culture in the presence of the sample is indicative of the presence of cytotoxic agents in the sample.

DETAILED DESCRIPTION OF THE INVENTION

This application relates to a method for testing of whole effluent toxicity, i.e., for toxicity of the combination of chemical compounds, both organic and inorganic which may be present in an effluent sample, and for the determination of component-toxicity associated with dissolved and particulate materials. In accordance with the invention, samples are tested without any requirement for concentration of the sample by combining the sample with a growing culture of particle-feeding flagellate protozoans. Suitable flagellates include bodonines such as *Bodo designis* and *Bodo caudatus*, retromonads such as *Scytomonaspusilla* and *Cercomonas longicauda*) and amoeba flagellates such as *Tetramitus rostratus* and *Chilodenella uncinata*?A preferred organism for use in the WET test of the invention is a culture of *Tetramitus rostratus*, and this organism will be used as the general, non-limiting example in the discussion which follows. *Tetramitus*, however, isunsuitable for use in WET testing of marine water samples (flagellates die in 10% sea water). *Bodo designis* and *Diplonema ambulator* are two species of nmarie flagellates which could be used in the invention for testing of marine and estuarine samples.

The same basic methodologies described below for *T. rostratus* can be employed when using other particle-feeding methodologies. Although somenvariations may be necessary for other species, it will be appreciated that these modifications are in the nature of routine optimization and are within the skill in the art.

*T. rostratus* has a complicated life cycle involving three distinct forms: flagellate, ameboid and cyst. The flagellate is used in the present invention. Cultures which remain indefinitely in the flagellate form can be obtained from plate cultures of the ameboid form. The ameboid forms are initially grown in liquid culture or on an agar plate in association with individual bacterial strains, including but not limited to *Klebsiella pneumoniae* or *Escherichia coil* which serve as a nutrient for the *T. rostratus*. The growth medium employed is selected to support the associated bacteria, e.g. P.M. agar for growth of either *K. pneumoniae* or *E. coli*. The ameba are then harvested and induced to transform to the flagellate form by removing the bacterial food source and reducing the oxygen tension to 0.3–0.4%. Single flagellates can then be isolated and grown up in liquid culture with bacteria such as *K. pneumoniae* as the sole food source in cultures useful for the present invention. These cultures have been found to be quite stable, with no reversion of the flagellate phenotype to the ameba phenotype having been observed in over 450 subcultures of flagellate populations reaching cell densities of up to $2 \times 10^7$ organisms/ml.

Preferred cultures for use in the invention are cultures which have been subcultured at least 5 to 6 times in bacteria/buffer medium following transfer from bacteria/nutrient medium, because these cultures exhibit the best growth rates. Further, the preferred cultures for use in the present invention contain *T. rostratus* flagellates at cell densities of from $1 \times 10^4$ and $1 \times 10^5$ organisms/ml.

*T. rostratus* flagellates have a rigid cytoskeleton, four flagellae, and a gullet. The presence of a gullet through which *T. rostratus* ingests its food is of special significance, because some of the toxic substances found within the whole effluent sample may be adsorbed onto small particles. *T. rostratus* can ingest these directly, thus providing a more complete evaluation of the toxicity of a whole effluent sample. Other particle-feeding flagellates may have different morphology, particularly in the structure of the gullet. For example, among the bodonines, the cytopharynx is lined with microtubules connected to one another and to the membrane, while in retromonads, the cytosomal lips are supported by three bundles of microtubules in eleven rows, cross connected by bridges which permit the opening of the orifice. Regardless of the morphological structure of the gullet, however, each facilitates the uptake of particulates, providing an ability to measure whole effluent toxicity.

Figure 6:
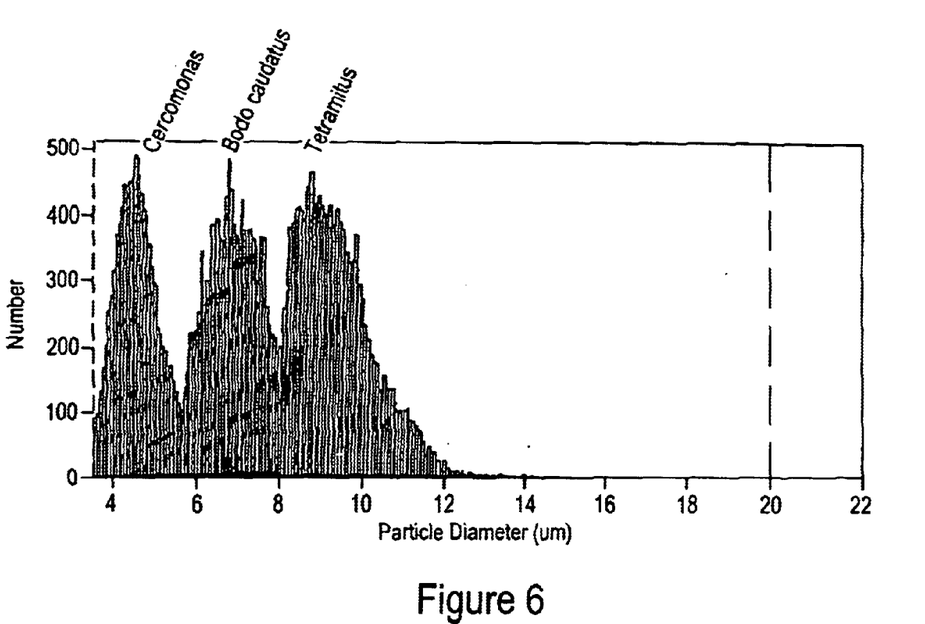
FIG. 6 shows size distributions for different species of particle-feeding flagellates.

It should be observed that the variations in flagellate morphology and in flagellate size offer an advantage because they permit the use of several species of flagellates to evaluate the association of toxic substances with particles of specific sizes. Thus, as shown in FIG. 6, *Cercomonas longicauda, Bodo caudatus* and *Tetramitus rostratus* exhibit three discrete size populations when evaluated with a Coulter Multisizer II. These size differences can be used as a "sieve" to obtain toxicity measurements that are graded based on the size of the particles with which the toxic substances are associated in the sample. In this case, the method of the invention would include monitoring the growth of two cultures of particle-feeding flagellates having different mean sizes in the presence of whole effluent and comparing the growth rate of the first and second cultures.

In addition to a stable, growing culture off lagellates such as *T. rostratus*, the cultures employed in the present invention contain bacteria and buffering components. Significantly, the culture does not contain any carbon source which is readily assimilable by bacteria. For this reason, there is essentially no risk of bacterial growth during the course of the test. Thus, the introduction of antibiotics, which is required to prevent the growth of contaminating bacteria during in situ air testing using the Ames test, is avoided.

In accordance with the method of the invention, a living culture of *T. rostratus* flagellates or other suitable organism as discussed above is combined with a whole effluent sample. Suitable starting samples include water samples, sewage samples, industrial effluent, and ocean or estuary samples. The starting sample is diluted to a series of dilutions for testing a range of concentrations and then added directly to a growing culture of the test organism. The growth of the organism is then monitored to assess the effect, if any, of the sample. Variation in growth as a result of toxic substance may be observed as a change in growth rate, as a change in means cell size or by other suitable measures. In the case of measurement of a growth rate, it will generally be necessary to compare the measured rate to a standard rate. With cell size, however, a decrease in cell size can be observed over time when a toxic substance is present without reference to a standard value.

In general, dilutions will result in samples with concentrations ranging between 10 and 90% of the original sample, and these dilutions made up to a volume of 900 uL are combined with 50 uL of concentrated *Klebsiella* suspension and 50 uL of flagellate culture ($2 \times 10^6$ cells/mL) as shown in Table 1. The target final concentration of flagellates in a 1 mL test culture is preferably $1.0 \times 10^5$ for *Tetramritus* flagellates.

TABLE 1

Preparation of Whole Effluent Dilutions

| Dilution-% | Sample | MS-1 | Klebsiella | Flagellate |
|---|---|---|---|---|
| 0 | — | 900 uL | 50 uL | 50 uL |
| 20 | 200 uL | 700 uL | 50 uL | 50 uL |
| 40 | 400 uL | 500 uL | 50 uL | 50 uL |
| 60 | 600 uL | 300 uL | 50 uL | 50 uL |
| 90 | 900 uL | — | 50 uL | 50 uL |

The slope of the dose response curve is proportional to the initial starting cell concentration. Lower starting cell concentrations produce steeper dose response curves. This reflects the actual starting concentration of toxicant per single cell. For cadmium chloride, the concentration which causes 20% inhibition in the rate of cell division (Slope Ratio=0.8) is $6-8\times10^{-5}$ ug/cell.

Figure 1:
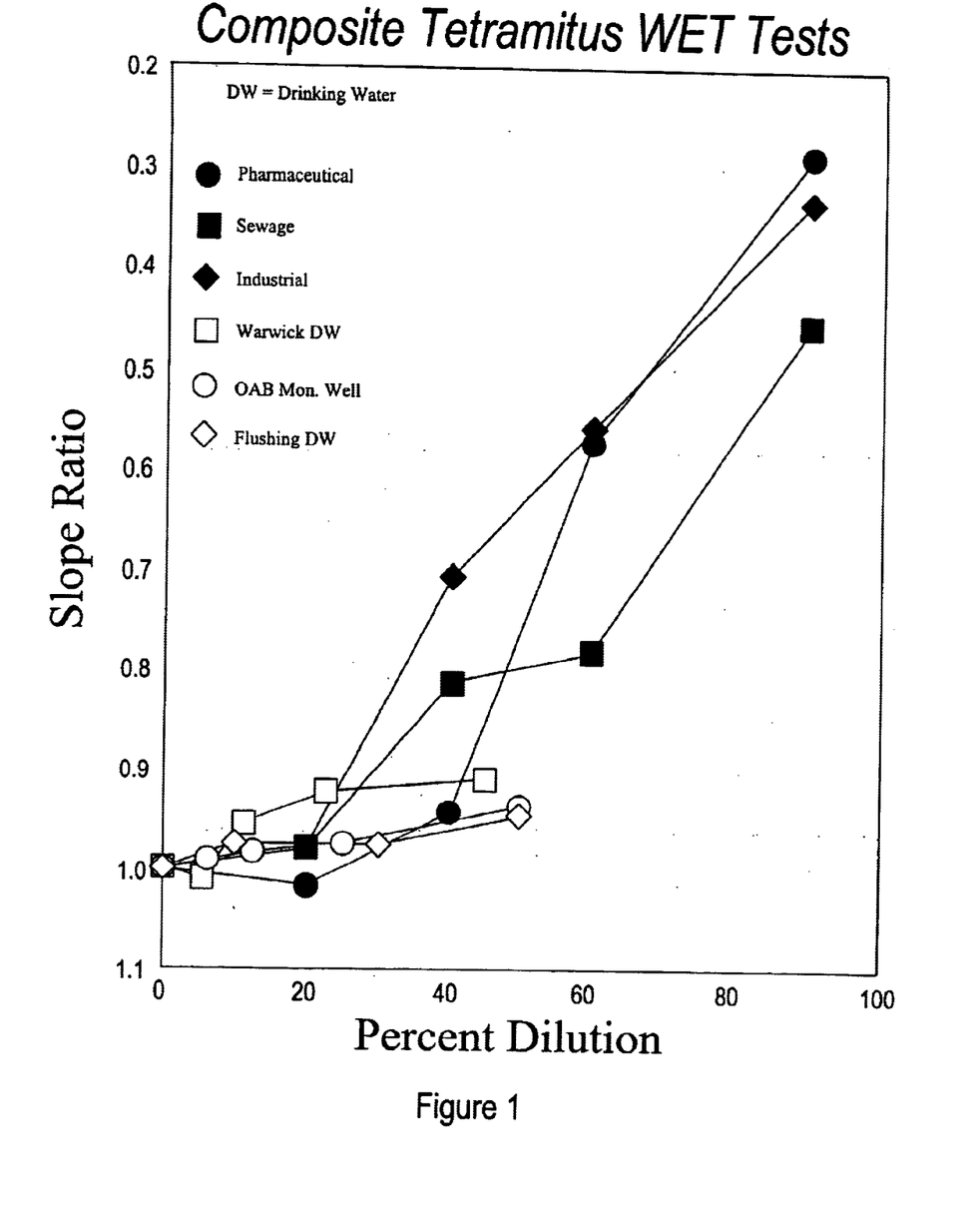
FIG. 1 shows a representative set of results for a test performed using *T. rostratus* to test for toxic substances in an effluent sample.

FIG. 1 shows a representative set of results for a test performed using *T. rostratus* to test for toxic substances in an effluent sample from a pharmaceutical plant, a secondary sewage sample, a sample from an industrial effluent stream, a sample from a monitoring well, a drinking water well and one from a municipal drinking water source. Each sample was diluted to a range of different concentrations and the growth rate of the culture when combined with each dilution of the sample. Each growth rate is then divided by a standard growth rate such that a non-toxic sample (no reduction in growth rate) will have a value of one (1) for ease of graphical presentation.

As shown in FIG. 1, the two industrial effluents and the secondary sewage sample all exhibited substantial toxicity. When these same samples were tested using two of the EPA accepted test organisms (Ceriodaphnia and Fat Head Minnow), however, only the sample of pharmaceutical effluent gave a positive result. Thus, the present invention is not only less expensive to perform than existing tests, it also provides greater sensitivity and faster response time (4 to 24 hours).

The method of the invention also provides a test for whole effluent toxicity which permits the evaluation of particle-size effects, and the association with toxic substances of particles of a particular size. Such information can be of significance in tracing the source of a particular set of toxic materials in a complex effluent, and may also have ramifications in the design of an abatement scheme. In this embodiment of the invention, the sample is filtered through one or more filters selected to exclude particulates of a desired size prior to the preparation of the dilutions. The filtrate is then tested for toxicity, and any difference between the observed toxicity for the filtered whole effluent sample and the unfiltered whole effluent sample is noted. If desired, the particulates removed by the filtration step can be evaluated separately, either by resuspending any materials captured by the filter or by recovering particulates from a larger aliquot of the whole effluent sample by centrifugation. For example, a whole effluent sample may be centrifuged for 6 hours at about 2,500×g, to form a pellet containing substantially all of the toxic substances likely to be present in the sample as particulates. The pellet is then reconstituted in buffer and combined with the growing culture of the test organism, for example *T. rostratus*. Once the sample is added, the growth rate of the organism is determined.

Thus, the method of the present invention permits the complete whole effluent sample and the fractions with potential toxic substances separated by particle size to be evaluated individually for any reduction in the growth of *T. rostratus*. As shown in the examples set forth below, any of several results may be obtained. Where the toxic substances are dissolved or are associated with particles smaller than the cut-off of the filter employed, there is no difference observed between the whole and the filtered sample. On the other hand, where the toxic substances are associated with particles that are retained by the filter a difference between the whole sample and the filtered sample will be observed. By resuspending the material captured by the filter and testing this fraction as well, a determination can be made as to whether or not there is any synergistic or non-additive relationship between particulate and dissolved substances. Use of different flagellate species may produce different toxicity patterns which can be used as a panel to assess the distribution of toxic substances within the sample. In general, smaller particles adsorb more toxicant per unit weight because of the increase in surface to volume ratio with decreasing particle diameter.

Determination of growth rates is accomplished in the same manner whether the sample added to the culture is unfiltered whole effluent, filtered whole effluent, a particulate portion of the whole effluent or a control solution. In general, growth rate is determined by measuring the number of cells in a volume of culture medium, i.e, the cell density at time intervals after addition of the test substance. Growth rate is determined from the slope of a line fit to these data values. The cell density may be measured in any of a variety of ways, e.g., using a hemocytometer or an electronic particle counter such as a Coulter Counter or laser sensing of suspended particles.

If the growth rate is lower than a standard value for the culture being used, then this is indicative of the existence of cytotoxic agents in the sample. Preferably, the standard value is determined using a simultaneous control to which either no sample is added or an equivalent volume of solvent used to dissolve the sample is added.

The results of the growth rate determinations are conveniently normalized by dividing each result by a standard value such that a sample with no toxic substances will produce a constant normalized value of 1 at all dilutions. In this way, the dose response effect of a toxic substance, i.e., the tendency of higher concentrations to be more toxic, can be easily seen.

EXAMPLE 1

Preparation and Evaluation of Tetramitus Cultures

*Tetramitus* flagellates were obtained from Dr. Frederick Schuster of Brooklyn College and maintained in association with *Klebsiella pneumoniae* in YP medium (0.5% Difco yeast extract and 0.5% Difco proteose peptone in water). *Tetramitus* cultures can also be purchased from the American Type Culture Collection, Rockville, Md. Flagellates inoculated from YP medium into bactena-buffer cultures usually take 5–6 subcultures before optimal growth conditions (mean division times of 7–8 hours at 27° C.) were observed. These cultures are maintained as backup cultures in case the standard bacteria-buffer cultures are lost.

Standard bacteria-buffer cultures of Tetramitus flagellates are grown in MS-1 buffer containing a dense suspension of *Klebsiella pneumoniae* (Kp). MS-1 contains 0.1 mM KCl, 0.3 mM $CaCl_2$, 0.3 mM $NaH_2PO_4$, 0.0008% pbenol red (pH indicator), and 1.4 mM $NaHCO_3$. The bicarbonate was added separately after autoclaving.

The bacteria (Kp) were grown for 20 hours in 300 ml of 2.5% Oxoid #2 nutrient broth (Unipath Ltd., CM67) in 2800 mL Fernbach Nephlo Flasks with baffles (Special Order from Bellco Glass). Bacterial growth was measured in a Klett Sommerson Nephelomter using a red filter. The Kp culture was divided into 6×50 mL sterile polypropylene centrifuge tubes (Corning #25330-50) and centrifuged for 10 minutes at 2500 RCF. The supernatant Oxoid Broth was decanted and the pellets resuspended in 40 mL MS-1 by vigorous mig on a vortex mixer. The wash volume of 40 mL was chosen to facilitate easy mixing and is not critical. The washed Kp are recentrifuged as above, the MS-1 supernatants are decanted and the pellets resuspended in 32 mL MS-1 per tube. 64 mL (2×50 mL tubes) of Kp suspension is resuspended in 32 mL baffled culture flasks and shaken at 26° C. and 180 rpm for periods of up to 20 days. These Kp suspensions are referred to as "soup flasks." The Kp soup serves as fresh medium for propagation of maintenance flasks. For toxicity testing, a 20× soup suspension is preparaed by centrifugation of 100 mL of Kp soup and resuspension of the pellets in 5 mL of MS-1 (See Table 1). Kp MS-1 is serially diluted by a factor of $10^7$ and 100 uL aliquots are spread on Oxoid #2 plates for enumeration and sterility checks. Oxoid #2 agar contains 15 g Oxoid #2 nutrient broth and 20 g og Oxoid or Difco Agar per 1000 mL of distilled water. Test tube slants of Oxoid agar are used for preparation of Kp slants. Inoculation of Oxoid broth cultures is achieved by touching a sterile 1 ml pipette to the Kp agar slant and then aseptic transfer of the Kp to the nephlo flask. Preparation of the soup flasks at least one day prior to use for testing allows for evaluation of the Kp preparation and prevents unnecessary loss of samples due to contamination or a bad batch of Kp. This method yields about $1.2 \times 10^{10}$ bacteria/mL.

Standard flagellate cultures were incubated in 125 ml baffled Erlenmeyer flasks in 10 ml of MS-1/Kp soup at 30° C. in a gyrarotary water bath shaker at 180 revolutions per minute.

Cell density was determined using a hemocytomter or by electronic particle counting.

1. Hemocytometer Counting-0.5 ml aliquots were withdrawn from the flagellate cultures and deposited in 1.0 mL volumetric tubes (Corning #5640-1) containing 2 drops of Lugol's iodine. The volume was adjusted to 1.0 ml and portions of the diluted cell suspension were transferred to a Levy Ultra Plane hemocytometer chamber. The average cell concentration was obtained from four separate determinations of 100 counts or more.

2. Electronic Particle Counting-cell concentrations were determined with the use of a Multisizer IIE Coulter Counter (Beckman-Coulter, Miami, Fla.). 0.2 ml aliquots were transferred to Folin-Wu tubes containing 30 ml of electrolyte (0.4% NaCl [w/v] in distilled water). The volume was adjusted to 35.0 ml by adding saline from a plastic wash bottle to the etched 35 ml volume line of the Folin-Wu tubes. The contents of each tube was agitated using a Vortex-Genie mixer, 20 ml portions were transferred to Coulter disposable counting cuvettes and 3 counts determined at lower channel $-6.01\mu$, upper channel $20.0\mu$ and mianometer selection of 500 uL. The narrow setting option of the Multisizer as used for optimal viewing of size distribution patterns. Use of the Coulter Accucomp® statistics report permitted evaluation of the growth status of each culture and allowed for quality control decisions on the use of cultures for seeding of test cultures. The growth status of individual cultures is correlated to the mean cell diameter and the coefficient of variation. On those occasions where growth is suboptimal, sample testing can be postponed for several hours or a day until satisfactory culture conditions in seed flasks are achieved.

EXAMPLE 2

Samples of two industrial effluents, one secondary sewage sample, one well water sample and 2 municipal drinking water samples were obtained. In order to maintain the original sample in MS-1 buffer, concentrated MS-1 components were added to 10 mL of neat sample according to the formulation presented in Table 2. This dilutes the original sample to about 90% of its original concentration to produce a whole effluent sample to be tested using the method of the invention.

TABLE 2

| Component | Volume |
| --- | --- |
| Water Sample | 10 mL |
| 0.1M $NaH_2PO_4$ | 30 uL |
| 0.1M $CaCl_2$ | 30 uL |
| 0.1M KCl | 10 uL |
| 0.5% Phenol Red Solution (Sigma P-0920) | 30 uL |
| 0.14M $NaHCO_3$ | 100 uL |

Test cultures of different effluent dilutions were prepared in 14 mL disposable tubes (Falcon #2057) according to the schedule described in Table 1. For each dilution, the slope of the growth curve was determined to provide a growth rate by monitoring cell concentration at two additional times (12–15 and 18–22 hours). These were then normalized by dividing the growth rate by the growth rate for the control. A plot of the resulting slope ratio as a function of dilution reflects the presence or absence of cytotoxic substances in the sample and can be summarized graphically as shown in FIG. 1. As shown, the industrial effluents and the secondary sewage were substantially inhibitory to growth of *T. rostratus*, and thus are determined to contain toxic substances. In addition, the well water sample also was determined to contain cytotoxic substances, although to a lesser extent.

EXAMPLE 3

Figure 2:
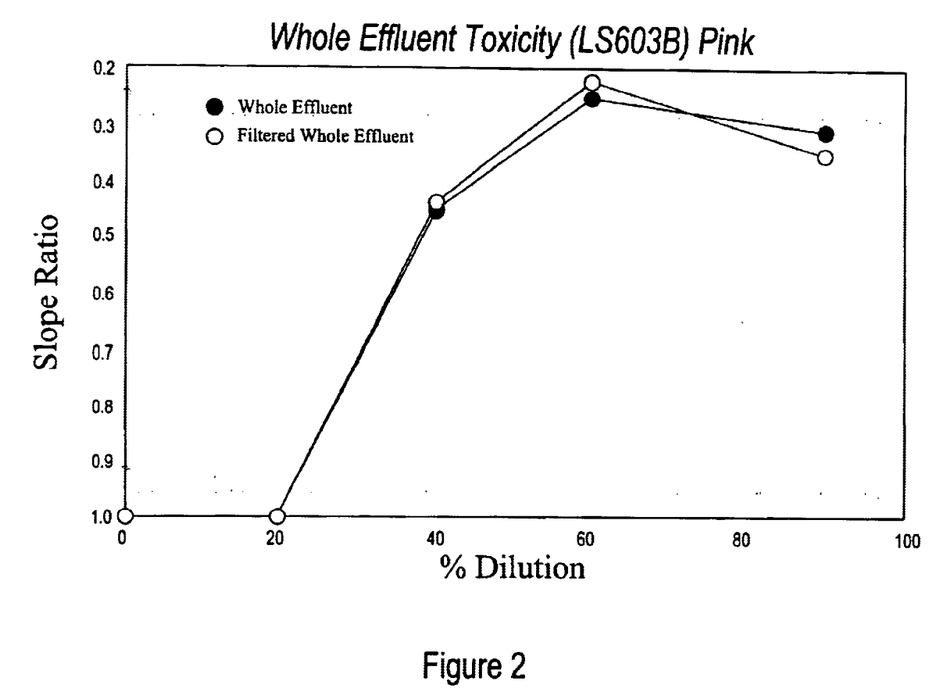
FIG. 2 shows results for a test in accordance with the invention with and without filtration.

An aliquot of the whole effluent sample prepared from effluent from a pharmaceutical plant from Example 2 was taken and divided into two parts. One part of the sample (5 ml) was then filtered through a Swinnex filter with a pore size of 0.45 $\mu$m. The whole effluent and the filtered whole effluent samples were then prepared as described in Table 1, and the dilutions were assessed for the presence of cytotoxic substances. The results are summary in FIG. 2, which shows that for this effluent, there is no discernable difference between the two. This means that the toxic substances in this case are not associated with particulates.

EXAMPLE 4

Figure 3A:
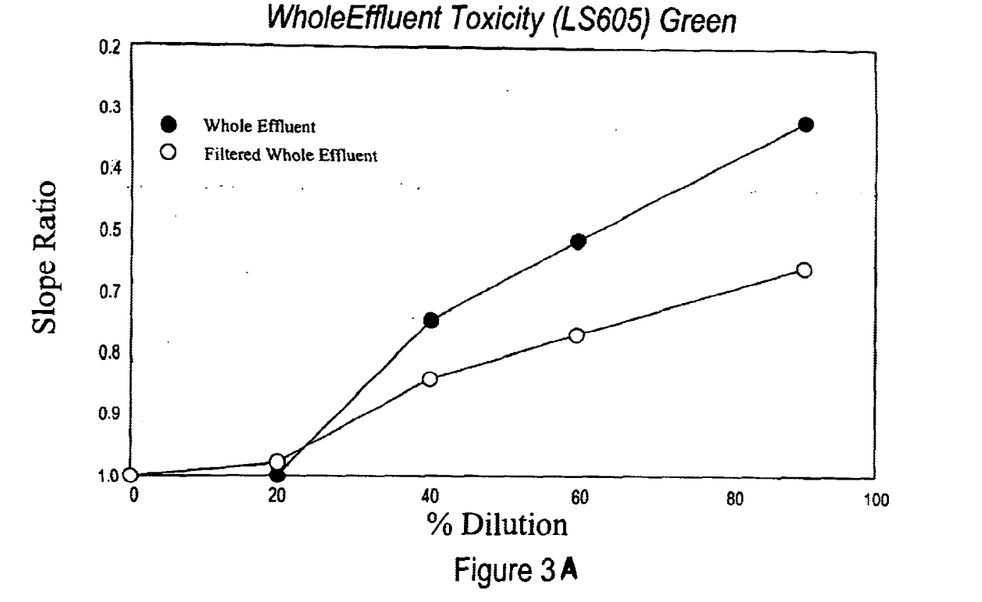
FIGS. 3A and B shows results for a test in accordance with the invention with and without filtration and for a particulate fraction.
Figure 3B:
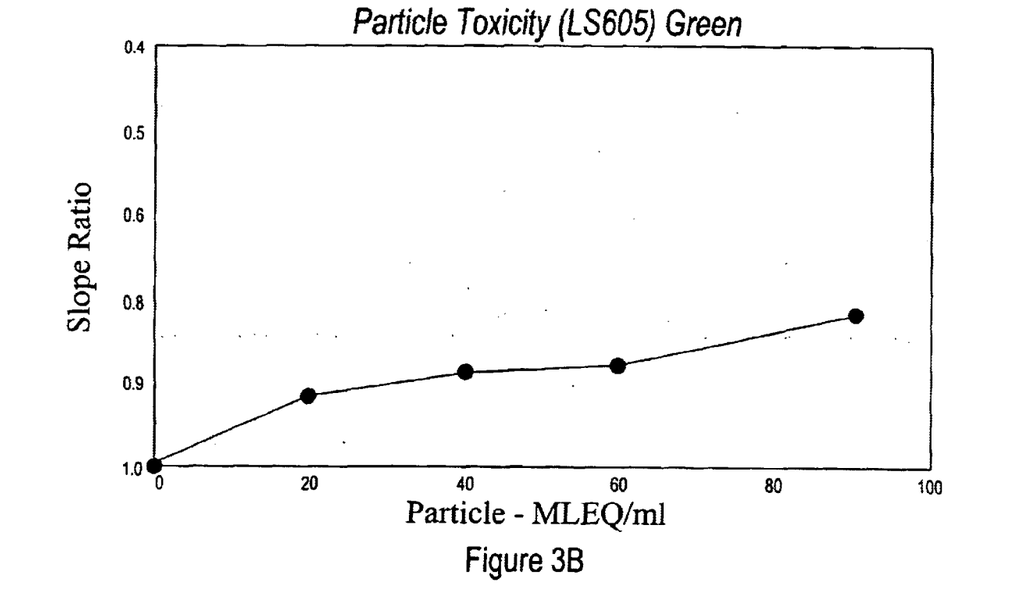

The procedure of Example 3 was repeated using the industrial effluent from Example 2. In this case, as summarized in FIG. 3A, there was an observed difference between the whole effluent samples and the filtered whole effluent. To evaluate the toxicity of the particulate materials two 180 ml aliquots of the whole effluent sample were centrifuged for 6 hours in a GLC-4 centrifuge @ about 2,500×g (RCF). The supernatant was decanted and the pellet was reconstituted with 3.6 ml MS-1 buffer to produce a concentrated particle fraction for testing having a particle concentration of 100 mL equivalents (MLEQ) per ml. The concentrated particle fraction was then tested for the presence of toxic substances, with the results shown in FIG. 3B. The filtered and particle toxicity levels apparently add up the total toxicity, thus indicating that there is little if any synergsim in this effluent.

EXAMPLE 5

Figure 4:
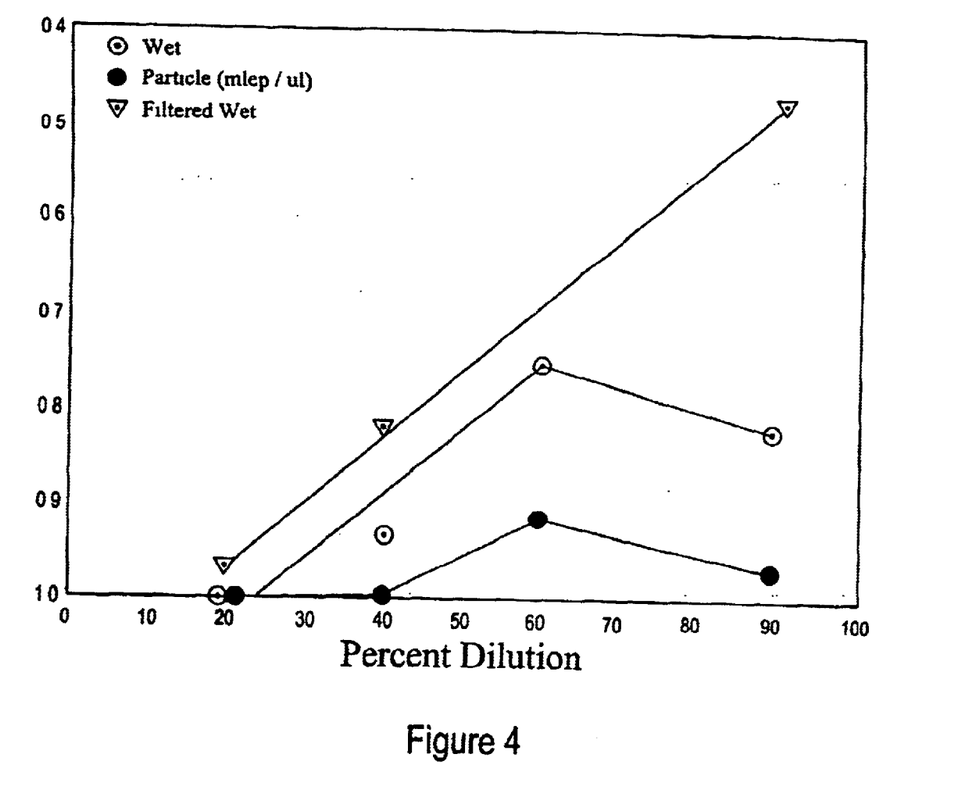
FIG. 4 shows results for a test in accordance with the invention with and without filtration.

The procedure of Example 3 was repeated using the secondary sewage from Example 2. In this case, as summarized in FIG. 4 the filtered dose response is linear to 90% dilution. On the other hand, both the unfiltered and the particle fraction show a break in the dose response curve at 60%, with higher levels of sample leading to no additional decrease in growth rate. This effect could be due to adsorption of toxic substances by the particles rendering them less effective, to saturation of the system at very high levels of toxic substances, or to the induction of additional detoxification pathways at high toxic substance levels. Understanding the particular reason for the observed non-linearity may be important in the development of a remediation strategy, yet existing tests would have generally failed to detect this effect. Indeed, this was a sample which the accepted tests found to be non-toxic.

EXAMPLE 6

Figure 5:
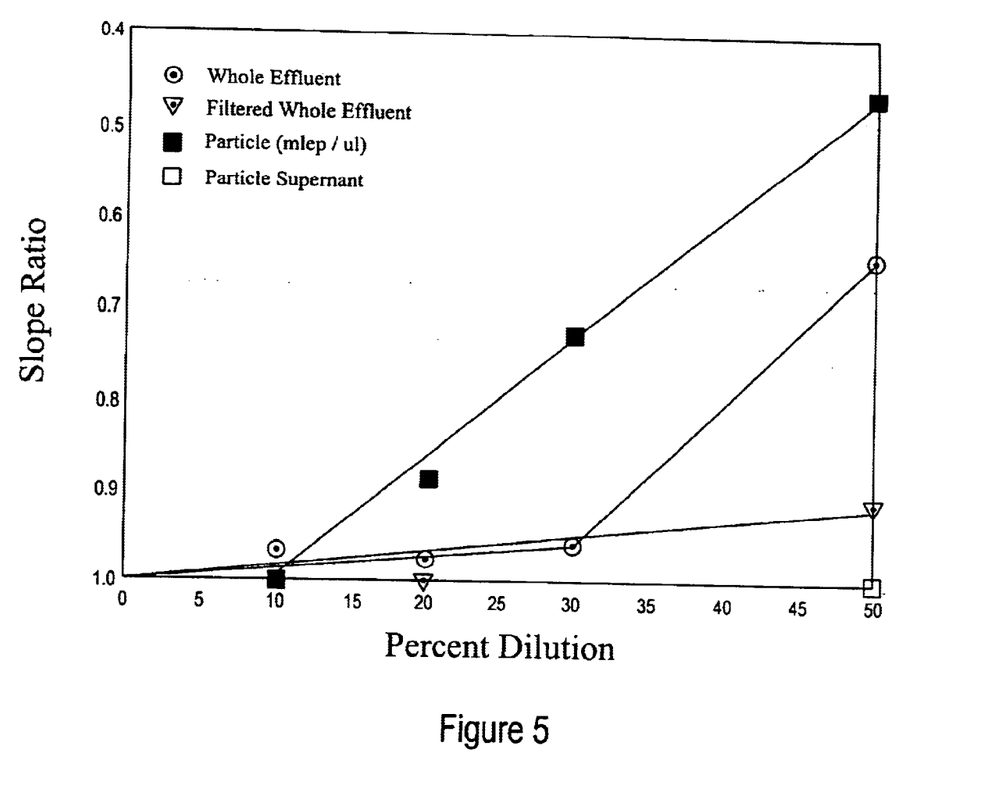
FIG. 5 shows results for a test in accordance with the invention with and without filtration.

The procedure of Example 3 was repeated using a pharmaceutical plant effluent (one of the industrial effluents) from Example 2. In this case, as summarized in FIG. 5, the whole effluent toxicity is substantially greater than the filtered whole effluent toxicity, and the evaluation of the particulate materials shows that they are the source of this toxicity.

EXAMPLE 7

Figure 7:
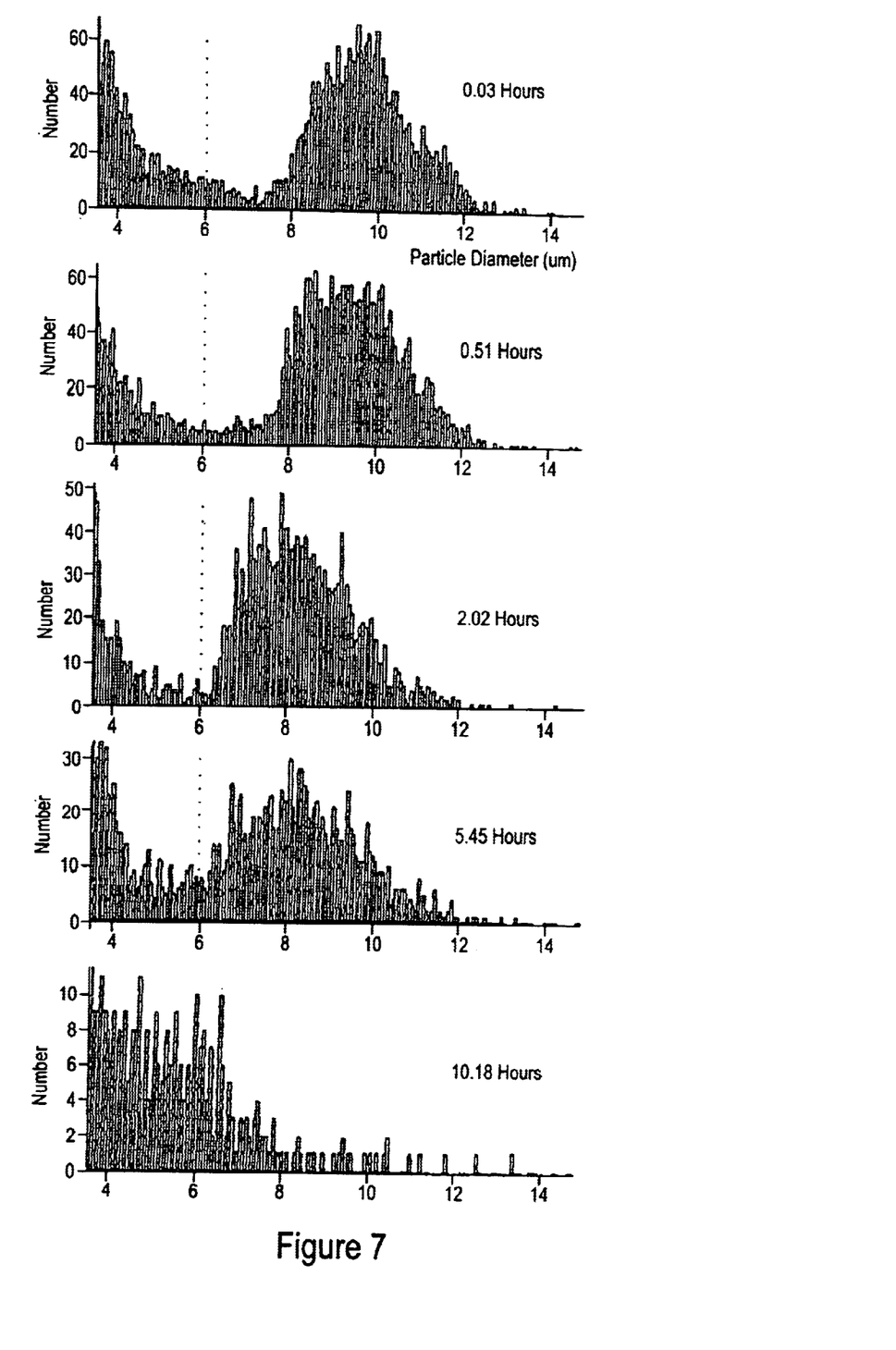
FIG. 7 shows variations in cells size as a measure of growth in the presence of toxin from spoiled fake crab meat.

The assay of the invention was used to measure the toxicity of an extract of spoiled fake crab meat by measuring the mean cell diameter of *T. rostratus* at intervals after exposure to the extract. The extract was prepared by hand-hoogenizing 1 gram, of spoiled fake crab meat in 20 mL MS-1 in a 40 mL all glass tissue grinder (Corning 441967). The suspension was centrifuged for 10 minutes at 2500 RCF and filtered through a cellulose acetate membrane filter (pore size 0.45 micron) to recover the supernatant. An aliquot of the supernatant was then added to a standard *T. rostratus* test mixture as described above. Cell diameters were measured using an AccuComp program of a Coulter Multisizer. The results are summarized in Table 3 and FIG. 7. As shown, the cell diameter decreased with increasing exposure time to the toxin. This highly toxic extract led to complete cell death in 10 hours. At lower concentrations, dose response curves are obtained in 10 to 20 hours.

TABLE 3

| Incubation Time (hrs) | Mean cell Diameter | Cells per ML (×350) |
|---|---|---|
| 0.03 | 9.53 | 1229 |
| 0.51 | 9.41 | 1342 |
| 2.02 | 8.34 | 1760 |
| 5.45 | 8.42 | 1148 |
| 10.18 | 5.56 | 377 |

What is claimed is:

1. A method for evaluating a whole effluent sample for the presence of cytotoxic substances comprising the steps of:
   (a) obtaining a liquid whole effluent sample for testing, said sample being suspected of containing a plurality of potentially cytotoxic substances;
   (b) combining a first aliquot of the liquid whole effluent sample directly with a culture of a particle-feeding flagellate said aliquot containing all of the potentially cytotoxic substances of the original sample obtained such that a measure of the toxicity of any combination of potentially cytotoxic substances can be obtained; and
   (c) monitoring the growth rate of the particle-feeding flagellate culture in the presence of the aliquot of the liquid whole effluent sample, wherein a decrease in growth rate of the culture in the presence of the liquid whole effluent sample is indicative of the presence of cytotoxic agents in the liquid whole effluent sample.

2. The method according to claim 1, wherein the particle-feeding flagellate is *Tetramitus rostratus* in flagellate form.

3. The method according to claim 1, wherein the particle-feeding flagellate is selected from the group consisting of *Chilodenella uncinata, Bodo caudataus, Cercomonas longicauda, Diplonema ambulator, Scytomonas pusilia* and *Bodo designis*.

4. The method according to claim 1, wherein a series of dilutions of the whole effluent sample is prepared and each dilution is individually combined with a culture of particle-feeding flagellate to determine a dose response curve.

5. The method according to claim 4, wherein the particle-feeding flagellate is *Tetramitus rostratus* in flagellate form.

6. The method according to claim 4, wherein the particle-feeding flagellate is selected from the group consisting of *Chilodenella uncinata, Bodo caudataus, Cercomonas longicauda, Diplonema ambulator, Scytomonas pusilia* and *Bodo designis*.

7. The method of claim 1, further comprising the steps of
   filtering a second aliquot of the whole effluent sample through a filter having a defined pore size to produce a filtered whole effluent sample from which particulate materials greater in size than the defined pore size have been removed;
   combining the filtered whole effluent sample with a second culture of particle-feeding flagellate;
   determining the growth of the second particle-feeding flagellate culture in the presence of the filter whole effluent sample; and
   comparing the growth of the second particle-feeding flagellate culture in the presence of the filtered whole effluent sample to the growth in the presence of the unfiltered whole effluent sample, wherein as difference in the growth is indicative of the presence of particulate toxic substances in the whole effluent sample.

8. The method of claim 7, wherein a series of dilutions of the filtered whole effluent sample is prepared and each dilution is individually combined with a culture of particle-feeding flagellate to determine a dose response curve.

9. The method according to claim 8, wherein the particle-feeding flagellate is *Tetramitus rostratus* in flagellate form.

10. The method according to claim 7, wherein the particle-feeding flagellate is *Tetramitus rostratus* in flagellate form.

11. The method according to claim 5, further comprising the steps of
    recovering a particulate fraction from an aliquot of the whole effluent sample;
    combining the particulate fraction with a third culture of particle-feeding flagellate;
    determining the growth of the particle-feeding flagellate culture in the presence of the particulate fraction; and
    comparing the growth of the particle-feeding flagellate culture in the presence of the particulate fraction to the growth in the presence of the unfiltered whole effluent sample.

12. The method of claim 11, wherein a series of dilutions of the particulate fraction is prepared and each dilution is individually combined with a culture of particle-feeding flagellate to determine a dose response curve.

13. The method according to claim 12, wherein the particle-feeding flagellate is *Tetramitus rostratus* in flagellate form.

14. The method according to claim 11, wherein the particle-feeding flagellate is *Tetramitus rostratus* in flagellate form.

15. The method of claim 1, further comprising the step of monitoring the growth of a second culture of particle-feeding flagellate in the presence of the whole effluent and comparing the growth of the first and second cultures, wherein the mean size of the flagellates in the first and second cultures is different.

* * * * *